United States Patent [19]

Di Giorgio et al.

[11] Patent Number: Plant 7,145

[45] Date of Patent: Feb. 6, 1990

[54] CARNATION NAMED KILLER

[75] Inventors: Antonio Di Giorgio; Renato Di Giorgio, both of San Remo, Italy

[73] Assignee: Laboratoire de Physiologie Vegetale, La Londe-Le Maures, France

[21] Appl. No.: 294,517

[22] Filed: Dec. 21, 1988

[51] Int. Cl.[4] ..... A01H 5/00

[52] U.S. Cl. ..... Plt./73

[58] Field of Search ..... Plt./73

*Primary Examiner*—Robert E. Bagwill

*Attorney, Agent, or Firm*—Charles W. Rummler

[57] ABSTRACT

A new standard carnation having a recurrent blooming habit and particularly distinguished by its profuse production of very large, Turkey Red flowers borne singly on long, strong, upright stems having moderately abundant foliage. This plant blooms profusely in its Spring, Midseason and Fall blooming periods with a vigorous growth habit, reaching a height of about 130 cm. at eight months of growth, resulting in a very favorable variety for commercial propagation for the production of cut flowers.

1 Drawing Sheet

BACKGROUND OF THE NEW PLANT

This new plant originated as a seedling derived from a hybrid produced by us at our nursery at San Remo, Italy, by crossing selected varieties of standard carnation plants from our collection of carnation plants maintained by us at our San Remo nursery for breeding purposes. The present plant was selected by us from seedlings of the said hybrid because of its profuse production of medium red flowers borne on long, strong flowering stems comprising a tall plant appearing to have a vigorous and rapid growth habit. This seedling was propagated by us at San Remo by means of cuttings with such favorable results that we directed that propagation be continued through several successive generations by means of successive cuttings and we thereby proved that the distinctive characteristics of the selected seedling would be retained from generation to generation and its homogeneity would thereby be assured.

This plant is now being grown on a commercial scale by Etablissements Barberet et Blanc, Laboratoire de Physiologie Vegetale, at 83250 La Londe-Les Maures, France.

DESCRIPTION OF THE DRAWING

Our new variety of standard carnation plant is illustrated by the accompanying full color photographic drawing, which shows stems of the new plant with blooms in several stages of maturity, with one of the stems bearing a bud just prior to the sepals dividing for the opening of the flower. The color rendition of this drawing is as close to that herein specified as is reasonably possible to obtain, considering the color involved, by professional photographic procedures.

DESCRIPTION OF THE NEW PLANT

The following is a detailed description of our new carnation variety determined by observation of plants grown in greenhouse and outside both at San Remo, Italy, and at La Londe-Les Maures, France, the color designation being according to The R.H.S. Colour Chart published by The Royal Horticultural Society at London, England.

THE PLANT

Origin: Seedling.

Parentage:

*Seed parent.*—Variety No. 64.

*Pollen parent.*—Variety No. 291. Both parents are unnamed and unpatented but are identified in our breeding records maintained in the office of our nursery at Via Villetta 41, 18038 San Remo, Italy.

Classification:

*Botanic.*—*Dianthus caryophyllus.*

*Commercial.*—Standard carnation.

Form: A tall, erect bush having at least four stems emitted near the ground.

Height: Average about 130 cm. at eight months of growth.

Main stem:

*Height.*—Less than 15 cm. due to pinching.

Branching character: This plant branches normally.

Growth: Vigorous, upright and rigid with good strength.

Foliage:

*Quantity.*—Moderately abundant.

*Number of leaves.*—More than 120.

*Leaf size.*—At the seventh node, the leaf average about 14.8 cm. long and about 1.1 cm. wide.

*Leaf shape.*—Oblong with inwardly rolled margins.

*Texture.*—Leathery.

*Ribs and veins.*—Hardly noticeable.

*Rachis.*—Hardly noticeable.

*Color.*—Both upper and under sides, 189-A.

*Leaflets.*—None.

THE BUD

Size: Large.

*Diameter.*—Averages about 2.2 cm.

*Length.*—Averages about 3 cm.

Shape: Ovoid.

Rate of opening: Normal.

Color of petals: When sepals first divided and when petals begin to unfurl, the color is the same as at full bloom.

Sepals:

*Number.*—Five.

*Shape.*—Generally ovate but joined together at their lower parts and having an acuminate apex.

*Character.*—The sepals are hooded over the bud before dividing and stand up when the flower opens.

*Color.*—Inside, 149-D/185-B. Outside, 137-A/185-B.

*Striae.*—Longitudinal.

Calyx:

*Size.*—Large.

*Shape.*—Bell-shaped.

*Splitting.*—There is little splitting.

*Aspect.*—Smooth.

Flower stem:

*Length.*—About 74.9 cm., in average (cut at the tenth node).

*Character.*—Rigid and erect.

*Color.*—189-A.

THE FLOWER

Blooming habit: Recurrent. This plant blooms profusely during its Spring, Midseason and Fall flowering periods.

Size of flower: Very large.

*Diameter.*—Averages about 9 cm.

*Depth.*—Averages about 6 cm.

Borne: Singly on long, rigid stems.

Shape: When bloom first opens, cup-shaped. When bloom matures, cup-shaped.

Petalage:

*Number of petals.*—About seventy-five, in average.

*Arrangement.*—Imbricated.

*Form.*—Fan-shaped with rounded edges and a serrated apex.

*Texture.*—Leathery.

*Aspect.*—Satiny.

*Color.*—Both outer petals and inside petals: Body — 46-B/46-C. Base — Greenish White. Reverse side — 46-B.

*Petaloids.*—Number: Less than ten. Size: Smaller than the petals. Color: The same as the petals.

Flower stem:

*Character.*—Upright with good strength.

Discoloration after full bloom: Very little.

Persistence: On the plant, the flowers hang on and dry.

Fragrance: Perceptible.

Lasting quality: As a cut flower, at least ten days in vase keeping.

THE REPRODUCTIVE ORGANS

Stamens:

*Number.*—Ten or eleven.

*Arrangement.*—Around the ovary.

*Anthers.*—Size: Less than 4 mm.

Pistils:

*Number.*—Two or three.

*Styles.*—Length: About 1.6 cm. Color: Reddish.

*Stigma.*—Color: Reddish.

Character of ovaries: Ribbed.

This new standard carnation variety most nearly resembles the variety 'Lontarion' (U.S. Plant Pat. No. 5,435). Compared with 'Lontarion', however, this new plant has a large flower and a more important number of petals.

We claim:

1. The new and distinct carnation cultivar, substantially as herein shown and described, particularly distinguished by its profuse production of very large Turkish Red flowers borne singly on long, strong stems of a tall plant having a vigorous growth habit.

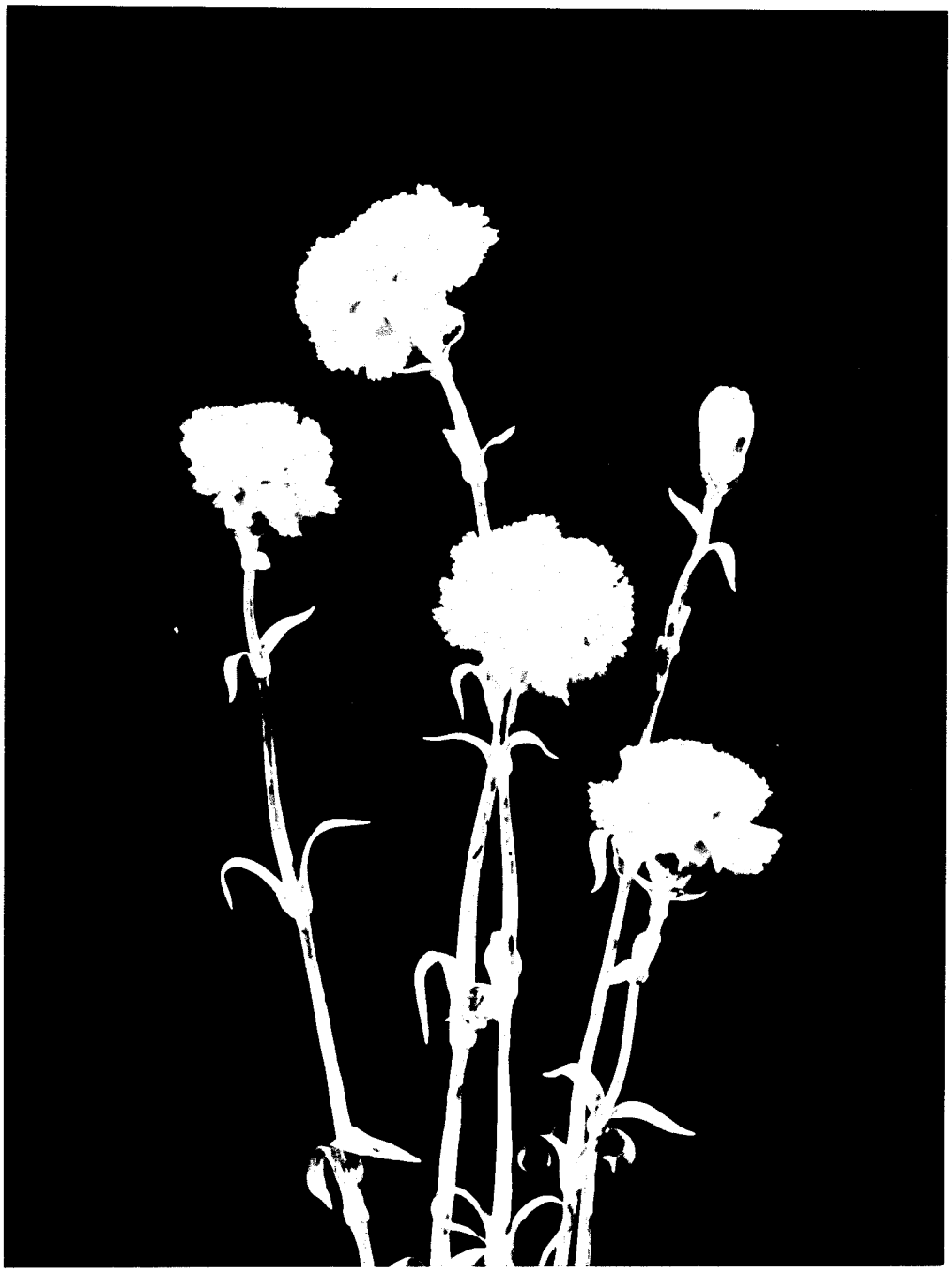

* * * * *